United States Patent [19]
Glover

[11] Patent Number: 6,017,546
[45] Date of Patent: Jan. 25, 2000

[54] WATER-IN-VOLATILE SILICONE EMULSION GEL COSMETIC

[75] Inventor: David Alan Glover, Midland, Mich.

[73] Assignee: Dow Corning Corporation, Midland, Mich.

[21] Appl. No.: 08/086,395

[22] Filed: Jul. 6, 1993

[51] Int. Cl.⁷ .............................. A61K 7/48; A61K 9/107
[52] U.S. Cl. ................... 424/401; 424/78.02; 424/78.04; 424/78.37; 514/941; 514/944
[58] Field of Search ................. 424/401, 78.02, 424/78.04, 78.37; 514/772.2, 941, 944

[56] References Cited

U.S. PATENT DOCUMENTS

| | | | |
|---|---|---|---|
| 5,015,469 | 5/1991 | Yoneyama et al. | 424/59 |
| 5,157,139 | 10/1992 | Legrow et al. | 556/470 |
| 5,160,730 | 11/1992 | Dubief et al. | 424/70 |
| 5,194,260 | 3/1993 | Grollier et al. | 424/71 |
| 5,216,033 | 6/1993 | Pereira et al. | 514/844 |
| 5,262,087 | 11/1993 | Tachibana et al. | 252/309 |
| 5,302,382 | 4/1994 | Kasprzak | 424/78.03 |
| 5,306,838 | 4/1994 | Shioya et al. | 556/445 |
| 5,387,417 | 2/1995 | Rentsch | 424/401 |
| 5,472,686 | 12/1995 | Tsubaki et al. | 424/59 |

*Primary Examiner*—Jeffrey C. Mullis
*Attorney, Agent, or Firm*—Jim L. DeCesare

[57] ABSTRACT

A water-in-volatile silicone emulsion gel having skin moisturizing qualities. The gel is formed by mixing an oil phase with a water phase. The oil phase contains a volatile silicone, a siloxane polyether, and an oil. The water phase contains water, a humectant, and an oxyethylene functional organosilane. Matching of the refractive index of the oil phase and the water phase results in the formation of a crystal clear gel having a viscosity in the range of 5,000 to 150,000 centistokes.

16 Claims, No Drawings

WATER-IN-VOLATILE SILICONE EMULSION GEL COSMETIC

BACKGROUND OF THE INVENTION

This invention is directed to a gel form of personal care cosmetic with moisturizing properties which are beneficial to the alleviation of dry skin conditions.

Inadequate hydration of the stratum corneum results in what is known as dry skin. About ten to twenty percent moisture is the minimum believed to be required in order to maintain the retention of normal skin softness and pliability. Accordingly, dry skin sufferers often supplement their own natural skin hydration by the application of consumer products containing humectants and moisturizers. Typically, humectants absorb moisture or aid another substance in the retention of moisture. Moisturizers supply moisture or restore moisture levels in the skin. The goal in either scenario is that of increasing the water content of the skin in order to maintain a soft and pliable skin condition. By including emollients, skin friction is reduced with the result that the skin is enabled to flex without breaking. This is often accompanied by a reduction or retardation in the water loss of the skin.

Of late, the concentration of clear gel forms of personal care products on cosmetic counters is on the rise. Products in clear gel form are very attractive in appearance and are generally regarded as having superior skin absorption characteristics in comparison to conventional emulsion products. Being single phase systems, clear gels have excellent stability. Since consumers perceive such products as being pure and hence safer, there is a growing demand in the marketplace for gel forms of products, and especially products with good shelf-life stability which is frequently a problem with clear products.

The water-in-volatile silicone emulsion gel cosmetic of the present invention is a product believed to fulfill that market need.

SUMMARY OF THE INVENTION

The invention relates to a water-in-volatile silicone emulsion gel having skin moisturizing qualities which is formed by mixing together an oil phase and a water phase. The oil phase contains a volatile silicone, a siloxane polyether, and an oil. The water phase contains water, a humectant, and an oxyethylene functional organosilane. The humectant should be a water soluble material having a refractive index above 1.35. Matching of the refractive index of the oil phase and the water phase results in the formation of a crystal clear gel having a viscosity in the range of 5,000 to 150,000 centistokes.

If the refractive index of the water phase is lower than the refractive index of the oil phase, the indices can be matched by the addition of more of the humectant. If the refractive index of the water phase is higher than the refractive index of the oil phase, the indices can be matched by the addition of more water.

In an alternate embodiment of the invention, the humectant is omitted from the water phase and the amount of the oxyethylene functional organosilane is increased. Crystal clear gels have been obtained with this technique in which the oxyethylene functional organosilane functions as the humectant.

These and other features, objects, and advantages, of the herein defined present invention will become more apparent from a consideration of the following detailed description thereof.

DETAILED DESCRIPTION OF THE INVENTION

As indicated above, the oil phase contains a siloxane polyether. One siloxane polyether suitable in accordance with the present invention is a compound having the formula:

One siloxane polyether of the present invention is a compound having the formula:

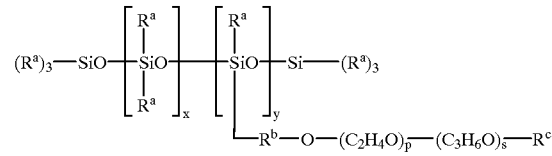

(I)

wherein $R^a$ is an alkyl group of one to six carbon atoms; $R^b$ is the radical $-C_mH_{2m}-$; $R^c$ is a terminating radical which can be hydrogen, an alkyl group of one to six carbon atoms, or an aryl group such as phenyl; m has a value of two to eight; p and s have values such that the oxyalkylene segment $-(C_2H_4O)_p-(C_3H_6O)_s-$ has a molecular weight in the range of 400 to 5,000; the segment preferably having fifty to one hundred mole percent of oxyethylene units $-(C_2H_4O)_p-$ and one to fifty mole percent of oxypropylene units $-(C_3H_6O)_s-$; x has a value of 80 to 120; and y has a value of 2 to 10.

Preferably, $R^a$ and the terminating radical $R^c$ are methyl groups; m is preferably three or four whereby the group $R^b$ is most preferably the radical $-(CH_2)_3-$; and the values of p and s are such as to provide a molecular weight of the oxyalkylene segment $-(C_2H_4O)_p-(C_3H_6O)_s-$ of between 1,000 to 3,000. Most preferably, p and s should each have a value of about 18 to 28.

Another suitable siloxane polyether which can be used in the formation of the oil phase is a compound having the formula:

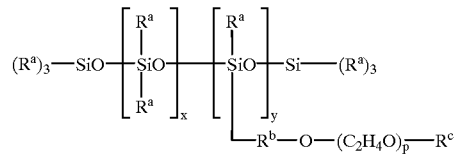

(II)

wherein $R^a$ is an alkyl group of one to six carbon atoms; $R^b$ is the radical $-C_mH_{2m}-$; $R^c$ is a terminating radical which can be hydrogen, an alkyl group of one to six carbon atoms, or an aryl group such as phenyl; m has a value of two to eight; p has a value of 8 to 16; x has a value of 6 to 12; and y has a value of 1 to 8.

It should be understood that in either Formula (I) or Formula (II) shown above, the siloxane-oxyalkylene copolymers may take the form of endblocked polyethers, in which the linking group $R^b$, the oxyalkylene segments, and the terminating radical $R^c$, occupy positions bonded to the ends of the siloxane chain, rather than being bonded to a silicon atom in the siloxane chain. Thus, one or more of the $R^a$ substituents which are attached to the two terminal silicon atoms at the end of the siloxane chain can be substituted with the segment $-R^b-O-(C_2H_4O)_p-(C_3H_6O)_s-R^c$ or with the segment $-R^b-O-(C_2H_4O)_p-R^c$. In some instances, it may be desirable to provide these segments at locations which are in the siloxane chain as well as at locations which are at one or both of the siloxane chain ends.

Methods of making silicone polyether compounds are known in the art, and are described in detail for example, in the volume "Chemistry and Technology of Silicones", Walter Noll, Academic Press Inc., 1968, Pages 373–376.

For the sake of brevity, the siloxane polyether of Formula (I) shall be referred to hereinafter as the "EO/PO Silicone Surfactant", whereas the siloxane polyether of Formula (II) shall be referred to as the "EO Silicone Surfactant".

Often, the "EO/PO Silicone Surfactant" is formulated as a blend containing about thirteen percent by weight of the "EO/PO Silicone Surfactant" active ingredient, and about eighty-seven percent by weight of a volatile cyclic silicone such as octamethylcyclotetrasiloxane, decamethylcyclopentasiloxane, or mixtures thereof.

In addition to water and a humectant, the water phase contains an oxyethylene functional organosilane. This water soluble material is a compound having the formula RSiR'$_3$ in which R is the radical —O(CH$_2$CH$_2$O)$_x$R"; R' is an R group or an alkyl radical having one to six carbon atoms; and R" is a radical selected from the group consisting of hydrogen; an alkyl group of one to six carbon atoms such as methyl, ethyl, propyl, and butyl; and an aryl group such as phenyl and benzyl. The integer x can have a value of six to thirty, but is preferably twelve to twenty.

One oxyethylene functional silane particularly preferred has the formula (CH$_3$)$_2$Si[O(CH$_2$CH$_2$O)$_{16}$H]$_2$. Such oxyethylene functional organosilanes may be prepared by methods involving the reaction of a silazane with an organic alcohol in the presence of an inorganic catalyst. One such method is described in detail in U.S. Pat. No. 5,157,139 issued Oct. 20, 1992, which patent is incorporated herein by reference.

The oil phase may contain other ingredients in addition to the siloxane polyether such as waxes and emollient oils. Waxes which may be employed include carnauba, beeswax, ceresin, paraffin, candelilla, bayberry, montan, spermaceti, castor wax, ozokerite, microcrystalline waxes, and Fisher-Tropsch waxes. Silicone waxes may also be used especially alkylmethylsiloxane wax materials such as polymethylstearylsiloxane. Typically, these silicone waxes are compounds having the formula Me$_3$SiO(Me$_2$SiO)$_x$(MeRSiO)$_y$SiMe$_3$ in which Me denotes methyl, R is C$_n$H$_{2n+1}$ in which n is an integer having a value of at least eighteen, x is 2 to 200 preferably about 3 to 70, and y is 3 to 40 preferably about 6 to 20. The silicone wax should have a melting point above an ambient or room temperature of about 20–25 degrees Centigrade (68–77° F).

Emollient oils which can be employed in the oil phase include mineral oil, peanut oil, sesame oil, avocado oil, coconut oil, cocoa butter, almond oil, safflower oil, corn oil, cotton seed oil, castor oil, olive oil, jojoba oil, paraffin oil, cod liver oil, palm oil, soybean oil, wheat germ oil, linseed oil, and sunflower seed oil; fatty acid esters such as isopropyl myristate, isopropyl palmitate, isopropyl stearate, butyl stearate, cetyl stearate, diisopropyl adipate, isodecyl oleate, diisopropyl sebacate, and lauryl lactate; fatty acids such as lauric, myristic, palmitic, stearic, oleic, linoleic, and behenic, acid; fatty alcohols such as lauryl, myristyl, cetyl, stearyl, isostearyl, oleyl, ricinoleyl, erucyl, and 2-octyl dodecanol, alcohol; lanolin and its derivatives such as lanolin, lanolin oil, lanolin wax, lanolin alcohols, lanolin fatty acids, isopropyl lanolate, ethoxylated lanolin, and acetylated lanolin alcohols such as ACETULAN®, a trademark and product of Amerchol Corporation, Edison, New Jersey; hydrocarbons such as petrolatum and squalane; and silicones such as non-volatile siloxane fluids and volatile siloxane fluids.

The non-volatile silicones useful in the oil phase are organic polysiloxanes which are film formers having a viscosity in the range of about 5 to as high as several million centistokes, but preferably about 100 to about 10,000 centistokes. A mixture of polysiloxanes having relatively higher and relatively lower viscosities may be employed. Such polysiloxanes have the repeating unit

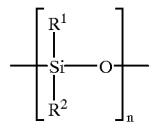

wherein n is an integer having a value greater than one; R$^1$ is an alkyl radical containing 1 to 7 carbon atoms, or a phenyl group; R$^2$ is hydrogen, an alkyl radical containing 1 to 7 carbon atoms, or a phenyl group. Illustrative non-volatile polysiloxanes are polydimethylsiloxane, polydiethylsiloxane, polymethylethylsiloxane, polymethylphenylsiloxane, polydiphenylsiloxanes, diphenylsilanediol, and copolymers of two or more of the foregoing siloxanes.

The non-volatile silicone film former can be blended with other types of silicone materials such as resins, and one particularly preferred silicone film former is a polydimethylsiloxane fluid having a viscosity of about one hundred centistokes measured at twenty-five degrees Centigrade, in admixture with TRIMETHYLSILOXYSILICATE. TRIMETHYLSILOXYSILICATE is the CFTA adopted name for a silicone resin of the formula [(CH$_3$)$_3$SiO$_{1/2}$]$_x$[SiO$_{4/2}$]$_y$ in which x and y are positive integers.

Another useful silicone film forming material for use in the oil phase is an ultra-high viscosity silicone gum. These silicone gums typically have the structure HOMe$_2$SiO(Me$_2$SiO)$_n$SiMe$_2$OH in which Me is methyl, and n is an integer having a value of at least one and which can be as much as 10,000.

Because of the high viscosity of these silicone gums, and for the purpose of facilitating their handling and processing, such gum materials are often provided in the form of a blend with another volatile or non-volatile low viscosity silicone such as CYCLOMETHICONE or a non-volatile linear silicone fluid having a viscosity of about 5 to 350 centistokes. The hydroxy terminated dimethylsilicone polymer has been assigned the adopted name DIMETHICONOL by The Cosmetics, Toiletries and Fragrance Association, Inc., Washington, D.C. (CTFA). Blends of that gum with a volatile low viscosity cyclic silicone have been assigned the adopted name CYCLOMETHICONE (and) DIMETHICONOL by the CTFA. Other blends of such silicone gums with non-volatile low viscosity linear silicones have been assigned the adopted name DIMETHICONE (and) DIMETHICONOL by the CTFA. Typically the DIMETHICONOL content of such blends is about 12 to 14 percent by weight, and the viscosity of the blended gum may range from about 500 to about 20,000 centistokes, generally in the range of 4,000 to 5,000 centistokes. The properties of these silicone gums can be modified by replacing one or more of the hydroxy or methyl groups with other substituents such as ethyl and vinyl for example.

The volatile silicone which may be employed in the oil phase is a low viscosity methylsilicone fluid. The volatile low viscosity methylsilicone fluid corresponds to the average unit formula (CH$_3$)$_a$SiO$_{(4-a/2)}$ wherein a is an integer having an average value of from two to three. The methylsilicone fluid contains siloxane units joined by Si—O—Si bonds. Representative units are $(CH_3)_3SiO_{1/2}$, $(CH_3)_2SiO_{2/2}$, $(CH_3)SiO_{3/2}$, and $SiO_{4/2}$. These units are present in molar amounts such that there is provided an average of from about two to three methyl groups per silicon atom in the methylsilicone fluid, whereby the methylsilicone fluid has a viscosity of less than about ten centistokes measured at twenty-five degrees Centigrade.

The volatile low viscosity methylsilicone fluid contains dimethylsiloxane units and optionally trimethylsiloxane units. Representative compounds are cyclopolysiloxane compounds of the general formula $[(CH_3)_2SiO]_x$, and linear siloxane compounds of the general formula $(CH_3)_3SiO[(CH_3)_2SiO]_ySi(CH_3)_3$, in which x is an integer having a value of from three to ten, and y is an integer having a value of from zero to about four.

The volatile low viscosity methylsilicones have boiling points generally less than about two hundred-fifty degrees Centigrade, and possess viscosities generally less than about is five centistokes measured at twenty-five degrees Centigrade. Most preferably, the viscosity is 0.65 to 5.0 centistokes.

The cyclopolysiloxane compounds have been assigned the adopted name "CYCLOMETHICONE" by The Cosmetics, Toiletries and Fragrance Association, Inc., Washington, D.C. (CTFA). Both the cyclopolysiloxanes and the linear siloxanes are clear fluids, and are essentially odorless, nontoxic, nongreasy and nonstinging. Cosmetically, these methylsilicone fluids are nonirritating to skin, and exhibit enhanced spreadability and ease of rub-out when applied. Once applied, the materials evaporate leaving behind no residue.

Volatile methylsilicone fluids which are operable in accordance with the present invention leave substantially no residue after thirty minutes at room temperature when one gram of fluid is placed at the center of a No. 1 circular filter paper having a diameter of 185 mm supported at its perimeter in open room atmosphere. By methylsilicone fluid is meant a composition containing two or more silicon atoms, all of which are bonded by way of at least one oxygen atom to at least one other silicon atom and at least one methyl radical, each silicon valence not satisfied by oxygen being satisfied by a methyl radical.

Representative volatile methylsilicone fluids found to be especially useful in accordance with the present invention are hexamethyldisiloxane which has a boiling point of 99.5 degrees centigrade and the formula $Me_3SiOSiMe_3$; hexamethylcyclotrisiloxane which has a boiling point of 133 degrees Centigrade and the formula $[(Me_2)SiO]_3$; octamethylcyclotetrasiloxane which has a boiling point of 171 degrees Centigrade and the formula $[(Me_2)SiO]_4$; and decamethylcyclopentasiloxane which has a boiling point of 205 degrees Centigrade and the formula $[(Me_2)SiO]_5$.

These volatile methylsilicone fluids may be used alone, or as mixtures in combinations of two or more. Mixtures of the methylsilicone fluids will result in a volatile material having an evaporating behavior different from any one of the individual methylsilicone fluids.

In some instances, it may be desirable to replace one or more of the methyl groups in the volatile methylsilicone fluid with other groups. Thus, there may be substituted groups such as alkyl radicals having two to twelve carbon atoms; aryl radicals having six to ten carbon atoms; amine groups; vinyl; hydroxyl; haloalkyl groups; aralkyl groups; and acrylate groups, for example.

Among the numerous humectants which may be employed as a constituent of the water phase are polyhydroxy alcohols such as sorbitol, glycerin, hexylene glycol, propylene glycol, and hexanetriol; sugar and starch derivatives such as alkoxylated glucose, and hydrolyzed mucopolysaccharides; D-panthenol, hyaluronic acid, lactamide monoethanolamine, acetamide monoethanolamine, urea, guanidine, glycolic acid and glycolate salts, lactic acid and lactate salts; and mixtures thereof. Most preferred are glycerin, propylene glycol, urea, hydrolyzed collagen, and sodium pyroglutamate ($C_5H_7NO_3Na$).

The humectant should be water soluble material having a refractive index above 1.35. Some representative refractive indices are glycerin (1.4744); propylene glycol (1.4325); hydrolyzed collagen (1.4930); and sodium pyroglutamate (1.4295).

In formulating the gel, other adjuvants can be included for the purpose of enhancing the aesthetic appeal of the product such as colorants, preservatives, and fragrances. Only adjuvants which do not effect the stability and clarity of the product should be selected.

Colorants include any of the United States Government Food & Drug Administration (FDA) certified inorganic and organic dyes and lakes such as carmine, iron oxide, mica, titanium dioxide, ultramarines, zinc oxide, bismuth oxychloride; and D & C Blue No. 1, D & C orange No. 5, D & C Red No. 6 Aluminum Lake, D & C Red No. 7 Calcium Lake, D & C Green No. 8, D & C Red No. 17, FD & C Blue No. 1, FD & C Red No. 3, FD & C Yellow No. 6, External D & C Violet No. 2, which are the CTFA adopted names of The Cosmetic, Toiletry, and Fragrance Association, Washington, D.C.

Preservatives which may be used are methyl paraben, ethyl paraben, propyl paraben, butyl paraben, diazolidinyl urea, imidazolidinyl urea, and mixtures thereof. Where an antimicrobial is required, materials such as Triclosan, Quaternium-15, chloroxylenol, and cetyl trimethyl ammonium bromide, may be employed.

Fragrances which may be used include natural products such as ambergris, benzoin, civet, clove, leaf oil, jasmine, mate', mimosa, musk, myrrh, orris, sandalwood oil and vetivert oil; aroma chemicals such as amyl salicylate, amyl cinnamic aldehyde, benzyl acetate, citronellol, coumarin, geraniol, isobornyl acetate, ambrette, and terpinyl acetate; and the various classic family perfume oils such as the floral bouquet family, the oriental family, the chypre family, the woody family, the citrus family, the canoe family, the leather family, the spice family, and the herbal family.

In preparing the individual oil phase and the water phase, the oil phase should constitute about 10 to 40 percent by weight of the composition, ideally about 25 percent by weight. The water phase on the other hand, should constitute about 60 to 90 percent by weight of the composition, ideally about 75 percent by weight. The oil phase itself is composed of 1 to 20 percent by weight of a volatile silicone; 2 to 20 percent by weight of the siloxane polyether; and 1 to 20 percent by weight of an emollient oil or other film forming material, preferably an organosilicon compound. The water phase should include 5 to 50 percent by weight of water; 1 to 10 percent by weight of the oxyethylene functional organosilane; and 5 to 50 percent by weight of a humectant or other water soluble material having a refractive index above 1.35.

The gel is formed by simply slowly mixing together the two phases under high shear.

The invention may be further illustrated in more detail by a consideration of the following example along with the accompanying table.

EXAMPLE I

Three crystal clear gel moisturizing compositions "A", "B", and "C" were prepared from an oil phase and a water phase containing the various ingredients shown below in the Table. The Table shows the amount of each ingredient in each phase expressed in grams. The ingredients in Oil Phase A were blended and mixed until uniform. The refractive index of Phase A was measured using a refractometer. The ingredients in Water Phase B were blended and mixed until uniform. The refractive index of Phase B was measured using a refractometer. If the refractive index of the water phase was found to be lower than the refractive index of the oil phase, the indices were matched by the addition of more of the humectant. If the refractive index of the water phase was higher than the refractive index of the oil phase, the indices were matched by the addition of more water. Water Phase B was added very slowly to Oil Phase A accompanied with high speed high shear mixing. Crystal clear high viscosity gels resulted having viscosities in the range of 5,000 to 150,000 centistokes. When applied to the skin, the gels possess moisturizing capabilities.

TABLE

| Phase | Ingredient | A | B | C |
|---|---|---|---|---|
| A | Volatile Cyclic Silicone | 10 | 10 | — |
| A | EO/PO Silicone Surfactant | 10 | 10 | 10 |
| A | Alkylmethyl Silicone Wax | 5 | — | — |
| A | Silicone Fluid/Resin Blend | — | 5 | 5 |
| A | Silicone Gum | — | — | 10 |
| B | Deionized Water | 35 | 35 | 35 |
| B | Oxyethylene Silane | 5 | 5 | 5 |
| B | Humectant | 35 | 35 | 35 |

In the Table, the humectant was glycerin, and each of the silicone and silane materials shown in the Table was a representative compound of one of the categories of organosilicon materials explained previously in detail.

EXAMPLE II

Example I was repeated and a fourth crystal clear gel moisturizing composition was prepared having the same formulation as composition "B" in the above Table, except that the humectant was omitted and the level of the oxyethylene functional organosilane was increased to forty. The results were the same as in Example I, and a crystal clear gel having skin moisturizing capabilities was obtained.

Other variations and modifications may be made in the compounds, compositions, and methods, described herein without departing from the essential features and concepts of the present invention. The forms of the invention described herein are exemplary only and are not intended as limitations on the scope of the invention as defined in the appended claims.

That which is claimed is:

1. A method of making a gel comprising (i) forming an oil phase having a volatile silicone, a siloxane polyether, and an emollient; (ii) forming a water phase having water, a water soluble humectant with a refractive index above 1.35, and an oxyethylene functional organosilane; (iii) measuring the refractive index of the oil phase and the water phase; (iv) matching the refractive indices of the oil phase and the water phase; (v) adding the water phase to the oil phase: and (vi) subjecting the phases to shear mixing; the volatile silicone being selected from the group consisting of cyclopolysiloxanes of the formula $\{(CH_3)_2SiO\}_x$ and linear siloxanes of the formula $(CH_3)_3SiO\{(CH_3)_2SiO\}_ySi(CH_3)_3$ in which x is three to ten and y is zero to four; and the oxyethylene functional organosilane has the formula $RSiR'_3$ in which R is the radical $-O(CH_2CH_2O)_xR''$; R' is R or an alkyl radical having one to six carbon atoms; and R" is selected from the group consisting of hydrogen, an alkyl group of one to six carbon atoms, and an aryl group; and x is six to thirty.

2. A method of moisturizing skin comprising applying to the skin an effective amount of a gel, and rubbing the gel into the skin, the gel being a composition made by (i) forming an oil phase having a volatile silicone, a siloxane polyether, and an emollient; (ii) forming a water phase having water, and an oxyethylene functional organosilane; (iii) measuring the refractive index of the oil phase and the water phase; (iv) matching the refractive indices of the oil phase and the water phase; (v) adding the water phase to the oil phase: and (vi) subjecting the phases to shear mixing; the volatile silicone being selected from the group consisting of cyclopolysiloxanes of the formula $[(CH_3)_2SiO]_x$ and linear siloxanes of the formula $(CH_3)_3SiO[(CH_3)_2SiO]_ySi(CH_3)_3$ in which x is three to ten and y is zero to four; and the oxyethylene functional organosilane has the formula $RSiR'_3$ in which R is the radical $-O(CH_2CH_2O)_xR''$; R' is R or an alkyl radical having one to six carbon atoms; and R" is selected from the group consisting of hydrogen, an alkyl group of one to six carbon atoms, and an aryl group; and x is six to thirty.

3. A method according to claim 1 in which the siloxane polyether is a compound having the formula:

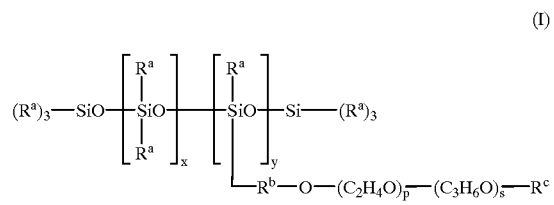

(I)

wherein $R^a$ is an alkyl group of one to six carbon atoms; $R^b$ is the radical $-C_mH_{2m}-$; $R^c$ is a terminating radical selected from the group consisting of hydrogen, an alkyl group of one to six carbon atoms, or an aryl group; m has a value of two to eight; p and s have values such that the oxyalkylene segment $-(C_2H_4O)_p-(C_3H_6O)_s-$ has a molecular weight in the range of 400 to 5,000; x has a value of 80 to 120; and y has a value of 2 to 10.

4. A method according to claim 3 in which $R^a$ and the terminating radical $R^c$ are methyl groups; m is three; and the values of p and s are such as to provide a molecular weight of the oxyalkylene segment $-(C_2H_4O)_p-(C_3H_6O)_s-$ of between 1,000 to 3,000.

5. A method according to claim 1 in which the emollient is an organosilicon compound selected from the group consisting of (i) an alkylmethylsiloxane wax having the formula $Me_3SiO(Me_2SiO)_x(MeRSiO)_ySiMe_3$ in which Me denotes methyl, R is $C_nH_{2n+1}$ in which n is an integer having a value of at least eighteen, x is 2 to 200, and y is 3 to 40; (ii) an ultra-high viscosity silicone gum having the formula $HOMe_2SiO(Me_2SiO)_nSiMe_2OH$ in which Me is methyl, and n is an integer having a value of 1 to 10,000; and (iii) a silicone film former which is a blend of a polydimethylsiloxane fluid and a silicone resin of the formula $[(CH_3)_3SiO_{1/2}]_x[SiO_{4/2}]_y$ in which x and y are positive integers.

6. A method according to claim 1 in which the oil phase is present in the amount of 10 to 40 percent by weight, and the water phase is present in the amount of 60 to 90 percent by weight.

7. A method according to claim 6 in which the oil phase includes 1 to 20 percent by weight of the volatile silicone, 2 to 20 percent by weight of the siloxane polyether, and 1 to 20 percent by weight of the emollient oil; and the water phase includes 5 to 50 percent by weight of water, 1 to 10 percent by weight of the oxyethylene functional organosilane, and 5 to 50 percent by weight of the humectant.

8. A method according to claim 7 in which the humectant is a compound selected from the group consisting of glycerin, propylene glycol, urea, hydrolyzed collagen, and sodium pyroglutamate.

9. A method of making a gel comprising (i) forming an oil phase having a volatile silicone, a siloxane polyether, and an emollient; (ii) forming a water phase having water, and an oxyethylene functional organosilane; (iii) measuring the refractive index of the oil phase and the water phase; (iv) matching the refractive indices of the oil phase and the water phase; (v) adding the water phase to the oil phase: and (vi) subjecting the phases to shear mixing; the volatile silicone being selected from the group consisting of cyclopolysiloxanes of the formula $\{(CH_3)_2SiO\}_x$ and linear siloxanes of the formula $(CH_3)_3SiO\{(CH_3)_2SiO\}_ySi(CH_3)_3$ in which x is three to ten and y is zero to four; and the oxyethylene functional organosilane has the formula $RSiR'_3$ in which R is the radical —$O(CH_2CH_2O)_xR''$; R' is R or an alkyl radical having one to six carbon atoms; and R" is selected from the group consisting of hydrogen, an alkyl group of one to six carbon atoms, and an aryl group; and x is six to thirty.

10. A method according to claim 9 in which the siloxane polyether is a compound having the formula:

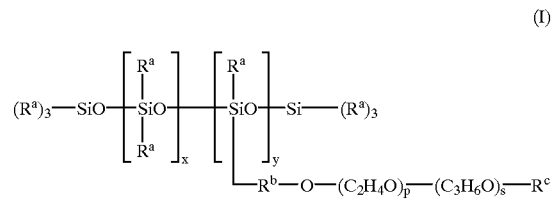

(I)

wherein $R^a$ is an alkyl group of one to six carbon atoms; $R^b$ is the radical —$C_mH_{2m}$—; $R^c$ is a terminating radical selected from the group consisting of hydrogen, an alkyl group of one to six carbon atoms, or an aryl group; m has a value of two to eight; p and s have values such that the oxyalkylene segment —$(C_2H_4O)_p$—$(C_3H_6O)_s$— has a molecular weight in the range of 400 to 5,000; x has a value of 80 to 120; and y has a value of 2 to 10.

11. A method according to claim 9 in which the emollient is an organosilicon compound selected from the group consisting of (i) an alkylmethylsiloxane wax having the formula $Me_3SiO(Me_2SiO)_x(MeRSiO)_ySiMe_3$ in which Me denotes methyl, R is $C_nH_{2n+1}$ in which n is an integer having a value of at least eighteen, x is 2 to 200, and y is 3 to 40; (ii) an ultra-high viscosity silicone gum having the formula $HOMe_2SiO(Me_2SiO)_nSiMe_2OH$ in which Me is methyl, and n is an integer having a value of 1 to 10,000; and (iii) a silicone film former which is a blend of a polydimethylsiloxane fluid and a silicone resin of the formula $[(CH_3)_3SiO_{1/2}]_x[SiO_{4/2}]_y$ in which x and y are positive integers.

12. A method according to claim 9 in which the oil phase is present in the amount of 10 to 40 percent by weight, and the water phase is present in the amount of 60 to 90 percent by weight.

13. A method according to claim 12 in which the oil phase includes 1 to 20 percent by weight of the volatile silicone, 2 to 20 percent by weight of the siloxane polyether, and 1 to 20 percent by weight of the emollient oil; and the water phase includes 5 to 50 percent by weight of water, and 5 to 50 percent by weight of the oxyethylene functional organosilane.

14. A gel comprising a composition made by (i) forming an oil phase having a volatile silicone, a siloxane polyether, and an emollient; (ii) forming a water phase having water, a water soluble humectant with a refractive index above 1.35, and an oxyethylene functional organosilane; (iii) measuring the refractive index of the oil phase and the water phase; (iv) matching the refractive indices of the oil phase and the water phase; (v) adding the water phase to the oil phase: and (vi) subjecting the phases to shear mixing; the volatile silicone being selected from the group consisting of cyclopolysiloxanes of the formula $[(CH_3)_2SiO]_x$ and linear siloxanes of the formula $(CH_3)_3SiO[(CH_3)_2SiO]_ySi(CH_3)_3$ in which x is three to ten and y is zero to four; and the oxyethylene functional organosilane has the formula $RSiR'_3$ in which R is the radical —$O(CH_2CH_2O)_xR''$; R' is R or an alkyl radical having one to six carbon atoms; and R" is selected from the group consisting of hydrogen, an alkyl group of one to six carbon atoms, and an aryl group; and x is six to thirty.

15. A gel comprising a composition made by (i) forming an oil phase having a volatile silicone, a siloxane polyether, and an emollient; (ii) forming a water phase having water, and an oxyethylene functional organosilane; (iii) measuring the refractive index of the oil phase and the water phase; (iv) matching the refractive indices of the oil phase and the water phase; (v) adding the water phase to the oil phase: and (vi) subjecting the phases to shear mixing; the volatile silicone being selected from the group consisting of cyclopolysiloxanes of the formula $[(CH_3)_2SiO]_x$ and linear siloxanes of the formula $(CH_3)_3SiO[(CH_3)_2SiO]_ySi(CH_3)_3$ in which x is three to ten and y is zero to four; and the oxyethylene functional organosilane has the formula $RSiR'_3$ in which R is the radical —$O(CH_2CH_2O)_xR''$; R' is R or an alkyl radical having one to six carbon atoms; and R" is selected from the group consisting of hydrogen, an alkyl group of one to six carbon atoms, and an aryl group; and x is six to thirty.

16. A method of moisturizing skin comprising applying to the skin an effective amount of a gel, and rubbing the gel into the skin, the gel being a composition made by (i) forming an oil phase having a volatile silicone, a siloxane polyether, and an emollient; (ii) forming a water phase having water, a water soluble humectant with a refractive index above 1.35, and an oxyethylene functional organosilane; (iii) measuring the refractive index of the oil phase and the water phase; (iv) matching the refractive indices of the oil phase and the water phase; (v) adding the water phase to the oil phase: and (vi) subjecting the phases to shear mixing; the volatile silicone being selected from the group consisting of cyclopolysiloxanes of the formula $[(CH_3)_2SiO]_x$ and linear siloxanes of the formula $(CH_3)_3SiO[(CH_3)_2SiO]_ySi(CH_3)_3$ in which x is three to ten and y is zero to four; and the oxyethylene functional organosilane has the formula $RSiR'_3$ in which R is the radical —$O(CH_2CH_2O)_xR''$; R' is R or an alkyl radical having one to six carbon atoms; and R" is selected from the group consisting of hydrogen, an alkyl group of one to six carbon atoms, and an aryl group; and x is six to thirty.

* * * * *